United States Patent [19]

Grimard

[11] Patent Number: 4,599,082
[45] Date of Patent: Jul. 8, 1986

[54] TWO-COMPONENT SYRINGE ASSEMBLY

[75] Inventor: Jean P. Grimard, Vif, France

[73] Assignee: Becton, Dickinson and Company, Franklin Lakes, N.J.

[21] Appl. No.: 640,434

[22] Filed: Aug. 13, 1984

[51] Int. Cl.$^4$ .............................................. A61M 5/00
[52] U.S. Cl. ..................................... 604/90; 215/355
[58] Field of Search ................ 604/82, 89, 90, 191, 604/218, 236, 238, 187; 215/6, 355

[56] References Cited

U.S. PATENT DOCUMENTS

| | | | |
|---|---|---|---|
| 2,549,417 | 4/1951 | Brown | 604/90 |
| 2,591,046 | 10/1948 | Brown | 604/90 |
| 2,607,341 | 12/1948 | Brown | 604/236 |
| 2,607,344 | 9/1952 | Brown | 604/90 |
| 3,330,282 | 9/1964 | Visser et al. | 604/90 |
| 3,477,431 | 11/1969 | Waleka | 604/89 |
| 3,941,128 | 3/1976 | Baldwin | 604/238 |
| 4,226,236 | 10/1980 | Genese | 604/89 |
| 4,394,863 | 6/1983 | Bartner | 604/90 |
| 4,439,184 | 3/1984 | Wheeler | 604/90 |
| 4,496,344 | 1/1985 | Kamstra | 604/90 |

Primary Examiner—Dalton L. Truluck
Assistant Examiner—Karen Kaechele

Attorney, Agent, or Firm—John L. Voellmicke

[57] ABSTRACT

A two-component syringe includes a barrel having a chamber for retaining fluid and a distal end of the barrel having a passageway therethrough communicating with the chamber. A by-pass stopper is slidably positioned in fluid-tight engagement inside the barrel. The stopper has a distal rib contacting the barrel, a recess on the proximal side of the rib and a groove in the rib for allowing fluid communication between the recess and the chamber. This groove is positioned angularly with respect to the longitudinal access of the barrel so that liquid passing therethrough is directed angularly with respect to the longitudinal axis of the barrel. The barrel also includes a raised peripheral portion serving as a by-pass and defining a by-pass zone. The by-pass zone is shorter than the length of the stopper along the longitudinal axis of the barrel. The by-pass is sufficiently long and raised enough to allow liquid to flow around the stopper between the proximal end of the stopper and the recess when the proximal end of the stopper is positioned in the by-pass zone. Also included is a piston slidably positioned in fluid-tight engagement inside the barrel. This piston is adapted to engage a plunger rod to facilitate its operation.

26 Claims, 17 Drawing Figures

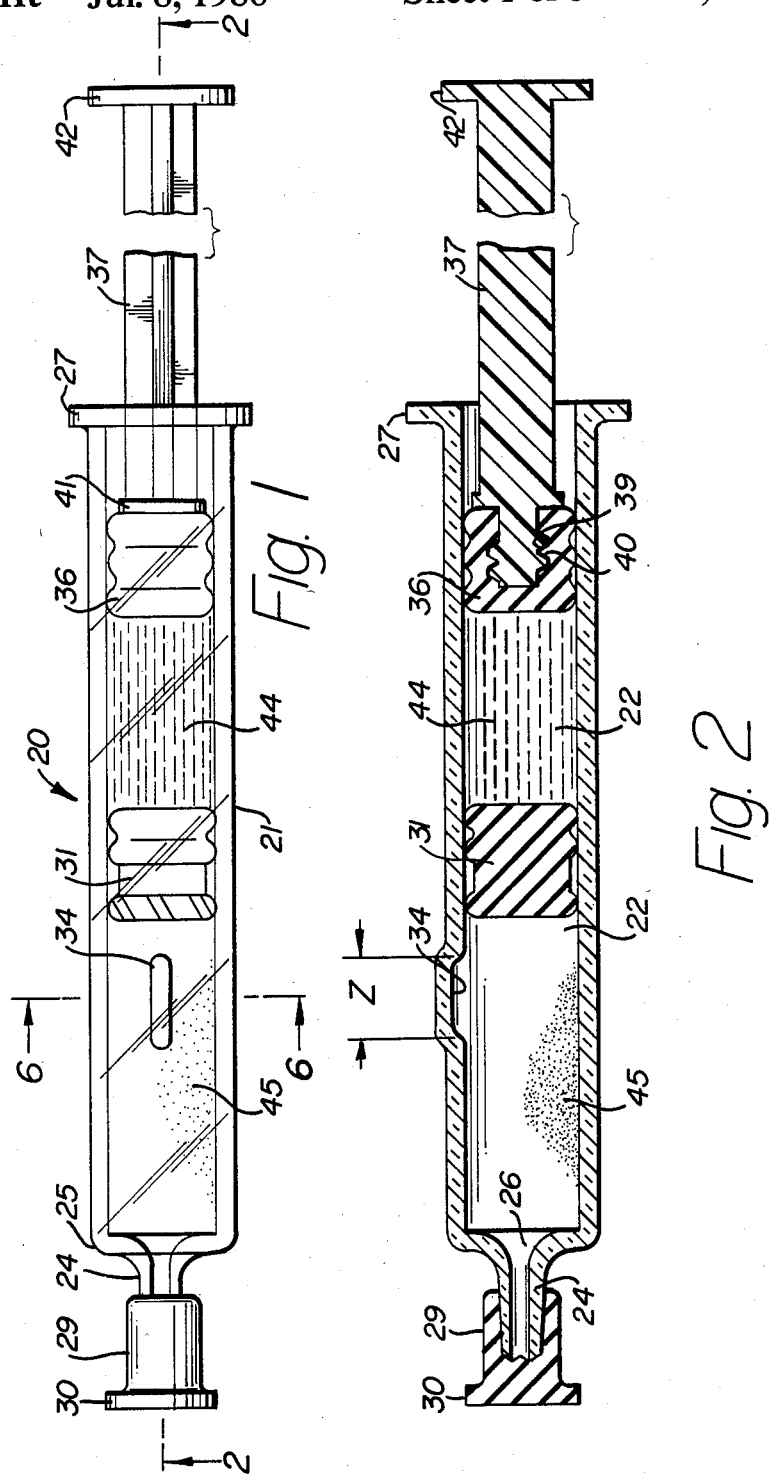

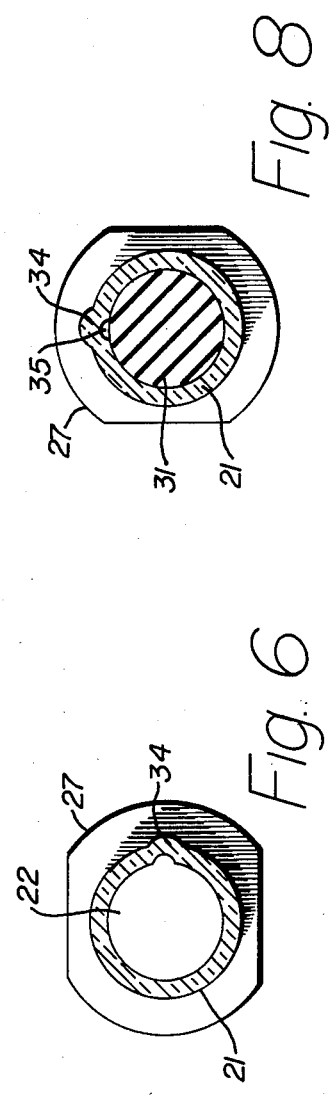
Fig. 6
Fig. 8
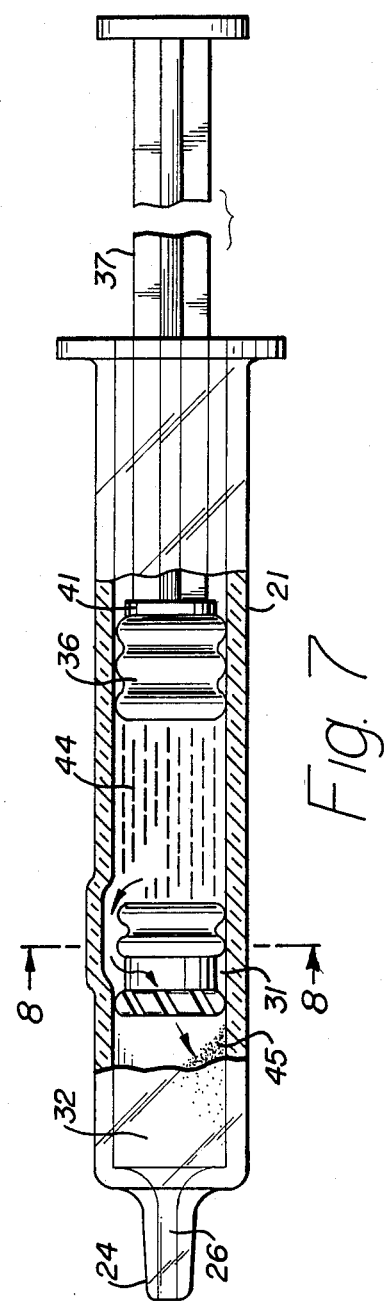
Fig. 7

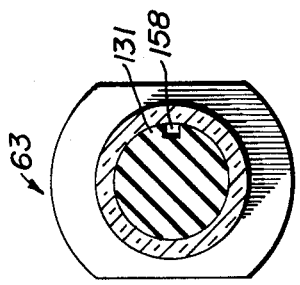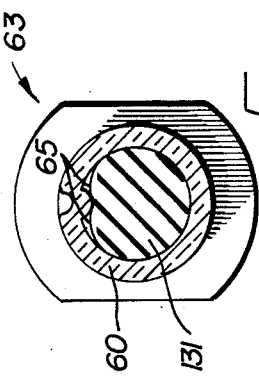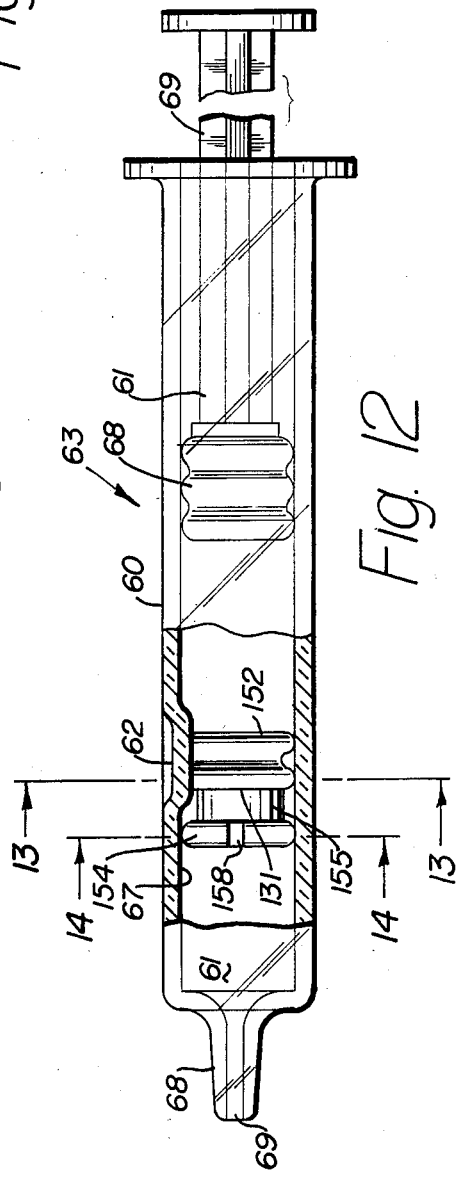

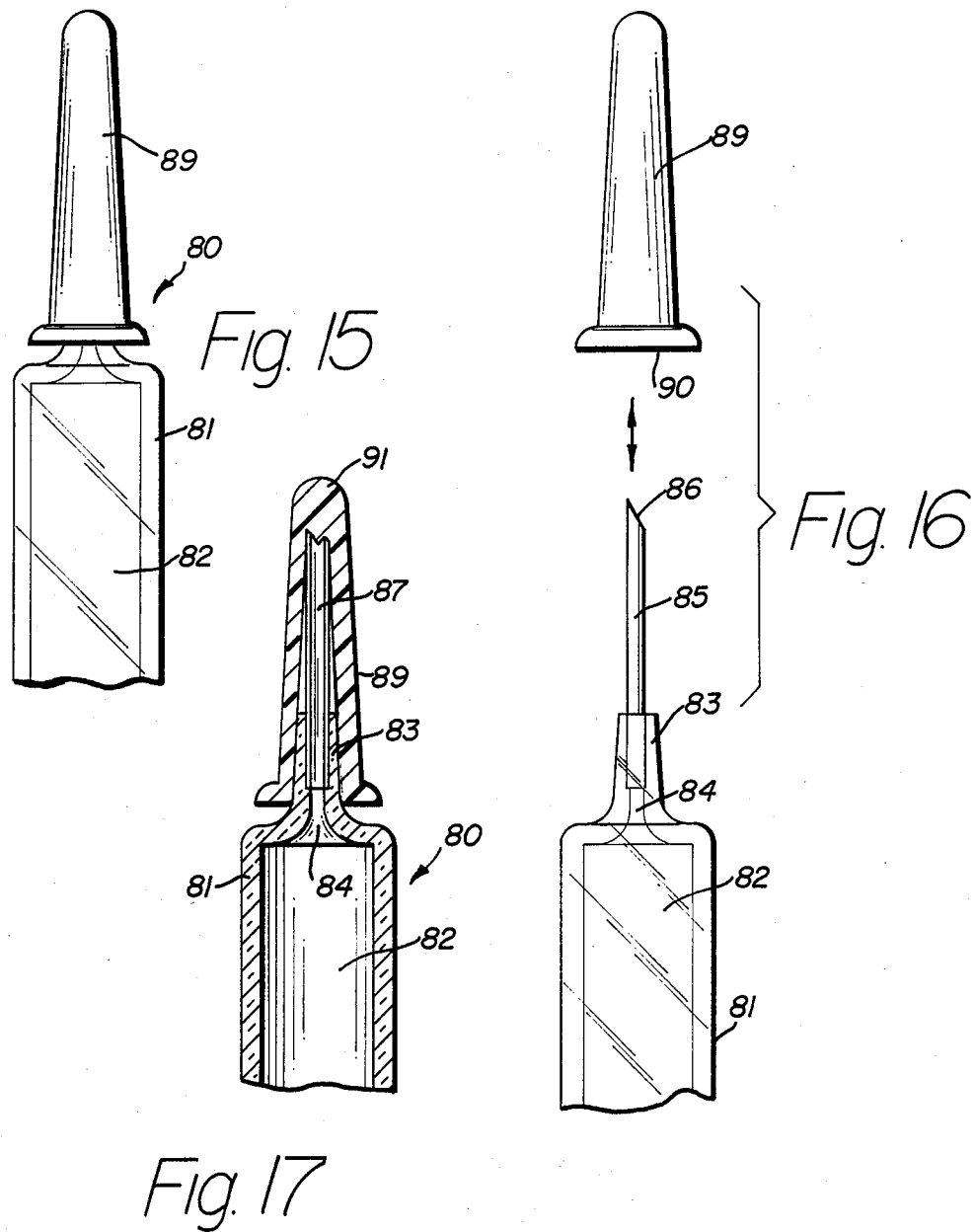

TWO-COMPONENT SYRINGE ASSEMBLY

BACKGROUND OF THE INVENTION

1. Field of the Invention.

The present invention relates to a syringe and more particularly concerns a two-component syringe.

2. Description of the Prior Art.

Some injectable medications have rapid loss of potency when they are in their ready-to-use form. In order to protect against the short shelf life of these medications, many of them are supplied in two-components, and they are mixed at the time of use. Two-component medication is commonly available in two vials with pierceable stoppers. A first vial typically contains a diluent such as sterile water and the second vial contains the active ingredients which may be in, for example, lyophilized form. To prepare the medication for use, the user pierces the stopper of the vial containing the water with a sterile syringe and needle assembly and withdraws the water into the syringe. The needle is then removed from the first vial and inserted into the second vial. Water is injected into this vial to mix with the lyophilized medication. The mixed medication is then withdrawn into the syringe for injection. When the injection is to be made into a vein, it is common practice to insert the needle into the patient and to withdraw the plunger rod slightly from the syringe barrel. If the needle is in a vein, a slight amount of blood will be drawn into the syringe. The visual sighting of the blood verifies that the needle is in a vein. This procedure is called the vein indication test. Also, when injection of medication into a vein or artery is not desirable, the vein indication test can be used to assure that the hypodermic needle is not in a vein or artery.

Use of the above-recited separate vials presents problems with respect to sterility since only the interior of the medication vial is sterile and bacteria from the exterior of the vials and the environment may be introduced into the medication during the mixing procedure. Also, at the areas where the cylindrical surfaces of the lumen of the hypodermic needle intersect the planes of its ground point, there are formed sharp edges that can potentially cut pieces of the rubber vial stopper away as the needle penetrates it. It should be noted that the potential for generating rubber particles varies between different needle point configurations. These pieces of rubber represent a potential health hazard if they pass along with the liquid medication into the patient's body. Further, cost is high since two separate sterile containers and a sterile syringe are normally required.

Brown (U.S. Pat. No. 2,607,344) teaches placing both components of the medication in a glass tube in which the components are separated by a stopper with a piston stopper sealing the end of the tube containing a liquid component and a flanged pierceable stopper sealing the end of the tube containing a powder component. Also, within the powder containing compartment, bounded by the stopper and the pierceable stopper, there is a longitudinally positioned groove projecting radially outwardly enlarging the inside diameter of the glass tubing. The groove is longer than the stopper so that when the stopper is positioned within the section of the tube containing the groove, liquid can flow around the stopper through the groove. Also provided is a separate barrel having an open proximal end adapted to accept the glass tube assembly and a distal end with a wall containing a cannular with opposed points. One end of the cannula projects into the barrel, and the other end projects outwardly away from the distal end of the barrel.

In use, the tube assembly of Brown is inserted into the barrel so that the portion of the cannula inside the barrel penetrates the pierceable stopper establishing fluid communication between the interior of the tube and the atmosphere. Then the piston stopper is forced inwardly pushing the liquid component of the medication and the stopper toward the distal end of the barrel. When the stopper is positioned within the by-pass, the liquid component flows around the stopper through the by-pass to mix with the powder component. To perform the vein indication test, the tube is withdrawn to terminate fluid communication with the cannula and then the outwardly facing portion of the cannula is inserted into the patient. Since the flange of the pierceable stopper is larger than the inside diameter of the barrel, further withdrawal of the tube from the barrel creates a reduced pressure zone between the exterior end of the pierceable stopper and the cannula causing blood to flow from the cannula into the barrel, outside of the tube assembly, if the cannula is lodged in a vein.

Genese (U.S. Pat. No. 4,226,236) teaches placing a liquid diluent and a solid medicament in a syringe barrel wherein the liquid diluent is contained between two stoppers and the solid medication is contained between one of the aforementioned stoppers and a hydrophobic filter which Genese suggests will not allow liquid to pass therethrough. This syringe contains an outwardly projecting by-pass on the side of the barrel. To mix the medicament and the diluent the user removes a ferrule and the closure cap on the distal end of the syringe assembly and then pushes the plunger rod, which is attached to the first stopper, inwardly. The movement of the first stopper forces the diluent and the intermediate stopper in a forward direction until the intermediate stopper is positioned in the area of the by-pass, and the diluent is then forced around the intermediate stopper through the by-pass and onto the solid medicament. It appears that when the diluent contacts the hydrophobic filter, no air or water is permitted to pass and, further, that whatever air remains in the syringe after the diluent contacts the hydrophobic filter is trapped within the syringe and cannot escape.

At this point, Genese teaches that the syringe is to be shaken to cause mixing of the two components. To use this syringe, a slidably mounted hollow piercing member is moved rearwardly to puncture the hydrophobic filter and to allow fluid communication between the interior of the syringe barrel and the interior of the hollow piercing member. The distal end of the slidable piercing member is shaped to allow attachment of a hypodermic needle assembly. With the hypodermic needle assembly attached, the remaining air and mixed medication can be expelled from the syringe. The Genese syringe has deficiencies in that it requires the puncturing of a syringe component in order to deliver the medication to the patient, and therefore it has the potential for generating foreign particles which could be injected into the patient. Further, Genese offers no teaching with respect to the vein indication test and the Genese syringe is complex having approximately 12 individual components. It also appears that the syringe taught by Genese will function only if the medication component between the stopper and the filter is not a liquid because the liquid in this area would seal the hydrophobic filter preventing air from escaping the preventing the movement of the stopper into the by-pass area.

It is undesirable to have a stopper or filter element within the syringe that must be punctured before medication can be discharged from the syringe because the puncturing can produce potentially harmful particles or debris which can then be injected into the patient. However, in the case of the syringe taught by Genese, if the filter were removed, the liquid may have a tendency to squirt from the by-pass directly into and/or out of the tip of the syringe. Accordingly, it is desirable to provide a two-component medication syringe which is configured to minimize loss through the syringe barrel tip while providing for the thorough mixing of the two medication components.

Presently pending U.S. patent application Ser. No. 536,927, filed Sept. 28, 1983, having a common Assignee herewith, also describes a two-component medication syringe.

Apparatuses and methods for the storage, mixing and administering of two-component medication have been addressed by the prior art, as alluded to, above. However, there is still a need for a simple, straightforward, reliable, easily fabricated syringe assembly for the storage, mixing and administering of two-component medications wherein one or both components are in liquid form. It is desirable that the syringe assembly minimize contamination potential by allowing the mixing and administering steps to be performed without puncturing stoppers or other barriers within the syringe or transferring the medication components through non-sterile barriers which are exterior to the syringe assembly. It is desirable that the syringe be configured to minimize medication loss during mixing and to promote thorough mixing of the medication components. It is also desirable that the syringe assembly be capable of easily performing the vein indication test.

SUMMARY OF THE INVENTION

The two-component syringe of the present invention comprises a barrel having a chamber for retaining fluid. A distal end of the barrel has a passageway therethrough for communicating with the chamber. A by-pass stopper is slidably positioned in fluid-tight engagement inside the barrel. This stopper has a distal rib at its distal end, a recess on the proximal side of the rib and fluid communication means in the rib for allowing fluid communication between the recess and the chamber. By-pass means is provided for allowing fluid to flow around the stopper between the proximal end of the stopper and the recess. Piston means is slidably positioned in fluid-tight engagement inside the barrel and is capable of engaging a plunger rod to facilitate its operation. The piston means is capable of moving fluid from the chamber through the passageway upon its movement toward the distal end, and the piston means is capable of facilitating the drawing of fluid into the chamber through the passageway upon its movement away from the distal end.

In accordance with another embodiment of the present invention, a two-component medication syringe includes an elongate substantially cylindrical barrel having a chamber for retaining fluid. A tip extends from the distal end of the barrel and has a passageway therethrough communicating with the chamber. The tip also has means for accepting a hypodermic needle. Sealing means is releasably connected to the tip for sealing the passageway. A by-pass stopper is slidably positioned in fluid-tight engagement inside the barrel. This stopper has a distal rib contacting the barrel, a recess on the proximal side of the distal rib and a groove in the distal rib for allowing fluid communication between the recess and the chamber. The groove is positioned angularly with respect to the longitudinal axis of the barrel so that liquid passing through the groove is directed angularly with respect to the longitudinal axis of the barrel. The stopper also has at least one proximal rib on the proximal side of the recess contacting the barrel. Also provided is a raised peripheral portion of the barrel serving as a by-pass and defining a by-pass zone. The by-pass zone is shorter than the length of the stopper along the longitudinal axis of the barrel. This by-pass is sufficiently long and raised to allow liquid to flow around the stopper between the proximal end of the stopper and the recess when the proximal end of the stopper is positioned in the by-pass zone. Also provided is a piston slidably positioned in fluid-tight engagement inside the barrel and adapted to engage a plunger rod to facilitate its operation. This piston is capable of moving fluid from the chamber through the passageway upon its movement towards the distal end, and it is further capable of facilitating the drawing of fluid into the chamber through the passageway upon its movement away from the distal end. A first liquid component of medication is contained within the chamber between the stopper and the piston. The stopper is positioned outside of the by-pass zone adjacent to the proximal end of the by-pass. A second component of medication is substantially within the chamber between the stopper and the distal end of the barrel.

Another aspect of the present invention is a by-pass stopper for use in a syringe having a substantially cylindrical barrel. This by-pass stopper includes a piston-like body, for slidable fluid-tight engagement inside the barrel, having a first end, a second end and a longitudinal axis therethrough. An annular rib at the first end and an annular rib at the second end of the body have an annular recess positioned therebetween. This recess has an outside diameter less than the outside diameter of the ribs. The rib at the first end includes a plurality of grooves for allowing fluid communication therethrough. The grooves are positioned angularly with respect to the longitudinal axis of the stopper.

In accordance with the principles of the present invention, a number of advantages and objectives are attained. Primarily, the present invention provides a simple, straightforward, reliable, easily fabricated syringe assembly for storing, mixing and administering two component medications wherein one or both of the components is in liquid form. The instant invention minimizes contamination potential by allowing the mixing and administering steps to be performed without puncturing stoppers or other barriers within the syringe or transferring the medication components through non-sterile barriers which are exterior to the syringe assembly. As will be hereinafter shown in more detail, the present invention provides a two-component medication syringe with structure that promotes a swirling action during the mixing of the two medication components. It further minimizes the potential of discharging medication through the syringe tip before mixing is complete and all gases are expelled from the syringe.

BRIEF DESCRIPTION OF THE DRAWINGS

FIG. 1 is a side elevation view of the preferred two-component medication syringe assembly of the present invention;

FIG. 2 is a cross-sectional view of the syringe assembly of FIG. 1 taken along line 2—2;

FIG. 6 is a cross-sectional view of the syringe assembly of FIG. 1 taken along line 6—6;

FIG. 7 is a side elevation view of the syringe assembly, similar to FIG. 2, with tip cap removed and interior section partially exposed, schematically showing the mixing of the two medication components;

FIG. 8 is a cross-sectional view of the syringe assembly of FIG. 7 taken along line 8—8;

FIG. 12 is a side elevation view of an alternative embodiment of the preferred two-component medication syringe barrel and by-pass stopper with a radially inwardly projecting by-pass and a longitudinally oriented by-pass stopper groove;

FIG. 13 is a cross-sectional view of the syringe barrel and by-pass stopper of FIG. 12 taken along line 13—13;

FIG. 14 is a cross-sectional view of the syringe barrel and by-pass stopper of FIG. 12 taken along line 14—14;

FIG. 15 is a partial side elevation view of another alternative embodiment of the two-component medication syringe assembly having a hypodermic needle cannula attached directly to the syringe tip;

FIG. 16 is the two-component medication syringe assembly of FIG. 15 illustrating the shield removed and separated from the syringe barrel; and FIG. 17 is a cross-sectional view of the two-component medication syringe assembly of FIG. 15.

DETAILED DESCRIPTION

Figure 3:
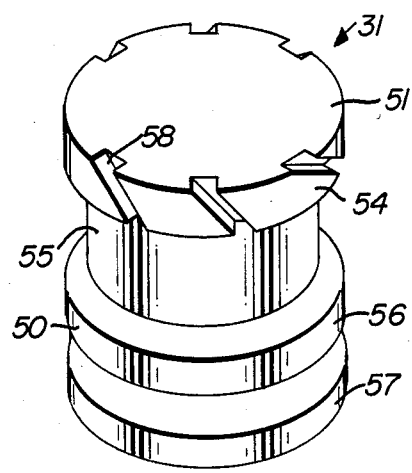
FIG. 3 is an enlarged perspective view of the preferred by-pass stopper of the present invention.
Figure 4:
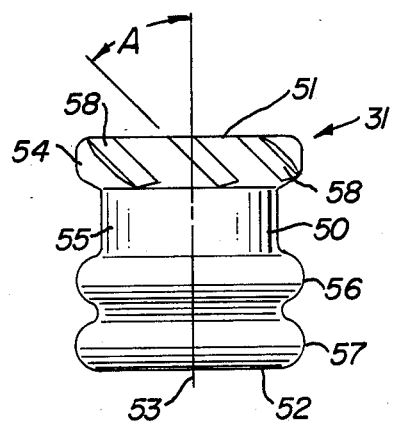
FIG. 4 is an enlarged side elevation view of the preferred by-pass stopper of FIG. 3.
Figure 5:
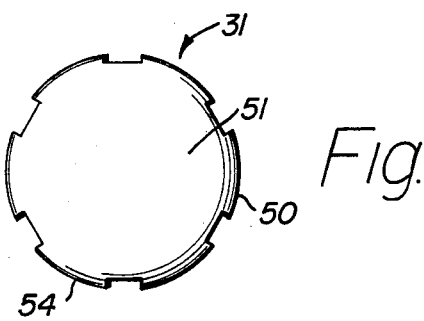
FIG. 5 is an enlarged top plan view of the preferred by-pass stopper of FIG. 3.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1 through 6, a two-component medication syringe 20 includes an elongate substantially cylindrical barrel 21 having a chamber 22 for retaining fluid. A tip 24 extends from a distal end 25 of the barrel and contains a passageway 26 therethrough communicating with chamber 22. For purposes of the description of the present invention, the term "distal end" is meant to refer to the end furthest from the person holding the syringe, whereas the term "proximal end" is meant to refer to the end closest to the holder of the syringe. Tip 24 is preferably adapted to accept a hypodermic needle, as will be described hereinafter. However, the tip may be adopted to engage other fluid transfer apparatus. A preferably resilient tip cap 29 is releasably connected to tip 24 and seals passageway 26 in an air-tight manner. Tip cap flange 30 is provided to facilitate installation and removal of the tip cap. A flange 27 may also be provided at the proximal end of the barrel to facilitate handling and positioning the syringe.

A resilient by-pass stopper 31 is slidably positioned in fluid tight arrangement inside the barrel. The by-pass stopper outside diameter is larger than the inside diameter of the barrel so that the stopper, when introduced into the syringe barrel, is compressed enough to provide adequate pressure between the syringe barrel and the stopper to seal this interface, but yet remains slidable within the barrel under the influence of force.

Preferred by-pass stopper 31 includes a piston-like body 50 having a distal end 51, a proximal end 52 and a longitudinal axis 53. An annular rib 54, positioned at the distal end, has an outside diameter larger than the inside diameter of barrel 21. Annular recess 55 is adjacent to distal rib 54. Proximal ribs 56 and 57, located at the proximal end, also have an outside diameter greater than the inside diameter of the barrel. The annular recess is preferably circular in cross-section, having an outside diameter of less than the outside diameter of each of the ribs and less than the inside diameter of the syringe barrel. Annular recess 55 preferably forms a continuous channel around the periphery of the stopper. The distal rib includes grooves 58 for allowing fluid communication between the volume described by the recess and the barrel, and the interior of the barrel. The grooves are preferably positioned angularly with respect to longitudinal axis 53 at angle A. While not limiting the present invention thereto, angle A is preferably within the range of about 30° to 80° with 60° being the most desirable angle. It is also within the purview of this invention to include a stopper wherein the individual grooves are at different angles with respect to the longitudinal axis. The angular orientation of grooves 58 causes liquid passing therethrough to be directed angularly with respect to the longitudinal axis, toward the interior wall of the barrel. As will be explained in more detail hereinafter, angularly positioned grooves 58 are an important feature of the present invention.

Syringe barrel 21 also includes a by-pass 34 preferably represented by a raised peripheral portion of the barrel extending radially outwardly and which defines by-pass zone Z along the barrel. The by-pass, as best shown in FIG. 6, effectively changes the inside diameter of the syringe barrel as measured through the by-pass zone. Also, the by-pass zone is shorter along the longitudinal axis of the barrel than the length of by-pass stopper 31 along the longitudinal axis of the barrel. As will be demonstrated later, the by-pass is sufficiently long and raised to allow fluid flow around the by-pass stopper, between the proximal end of the stopper and the recess, when the proximal end of the stopper is positioned within the by-pass zone. Although the by-pass preferably extends substantially in axial alignment with the longitudinal axis of the barrel, it may also be positioned in an angular relationship with respect to the longitudinal axis of the barrel.

A resilient piston 36 is slidably positioned in fluid-tight engagement inside the barrel. Piston 36 engages a rigid plunger rod 37. In the preferred embodiment, the stopper contains internal thread 39 which can engage external thread 40 on the plunger rod, when assembled as illustrated in FIG. 2. The plunger rod is accessible outside of the proximal end of the barrel and is provided to move the piston along the barrel to force fluid into or out of the chamber through the passageway. Disc-shaped plunger rod flange 42 is provided as a convenient structure for applying forces to move the plunger rod with respect to the syringe barrel. Piston flange 41 on the plunger rod is provided to supply a large surface area to transmit force from the plunger rod to the piston, in a direction toward the piston, without damaging the piston. The plunger rod can be installed when the syringe is assembled, or it may be provided as a separate unattached component which is engaged to the piston at the time of use. It will be apparent to one skilled in the art that numerous constructions can be used to join a piston and a plunger rod and that the arrangement described above is exemplary of these many possibilities. Also, it is within the purview of this invention to include a one-piece plunger rod-piston assembly.

The preferred embodiment of the instant invention contains two components of a medication which will be mixed at the time of use. Although this preferred embodiment is described in terms of a mixing syringe for medication, it is within the purview of this invention to include a syringe for mixing non-medication components which, because of their properties, must be contained separately until time of use, for example, the separate chemical components of an epoxy adhesive. A liquid first component of medication 44 is contained within the proximal end of chamber 22 between by-pass stopper 31 and piston 36. Note that the by-pass stopper is positioned outside of the by-pass zone adjacent to the proximal end of the by-pass. A second component of medication 45 is contained within the distal end of chamber 22, between by-pass stopper 31 and the distal end of the barrel. The second component of medication may be in the form of liquid, liquid soluble powder or solid, or combinations thereof. The preferred embodiment is described with the second component being a powder.

It should be noted that minimal force is required to move a resilient piston along a barrel when it is well lubricated with, for example, a medical grade silicon lubricant, or when the liquid being injected acts as a lubricant. However, when the piston remains in one position, even for a short period of time, the pressure exerted between the piston and the syringe barrel tends to force liquid or lubricant out of the interface between the piston and the barrel. As a result, the amount of force required to start the piston moving along the syringe barrel increases dramatically. This increased force is called the breakout force. For many syringes, the breakout force is so high that if the user initially pulls on the plunger rod, it will disengage from the piston. In the instant invention, piston flange 41 allows the user to provide more force to the piston, in the direction toward the piston, than could be applied by the plunger rod in a direction away from the piston, to facilitate overcoming the breakout force and moving the piston. It can be seen that the problem with breakout force is compounded where, as with the instant invention, there is a piston and a stopper to be moved.

Figure 9:
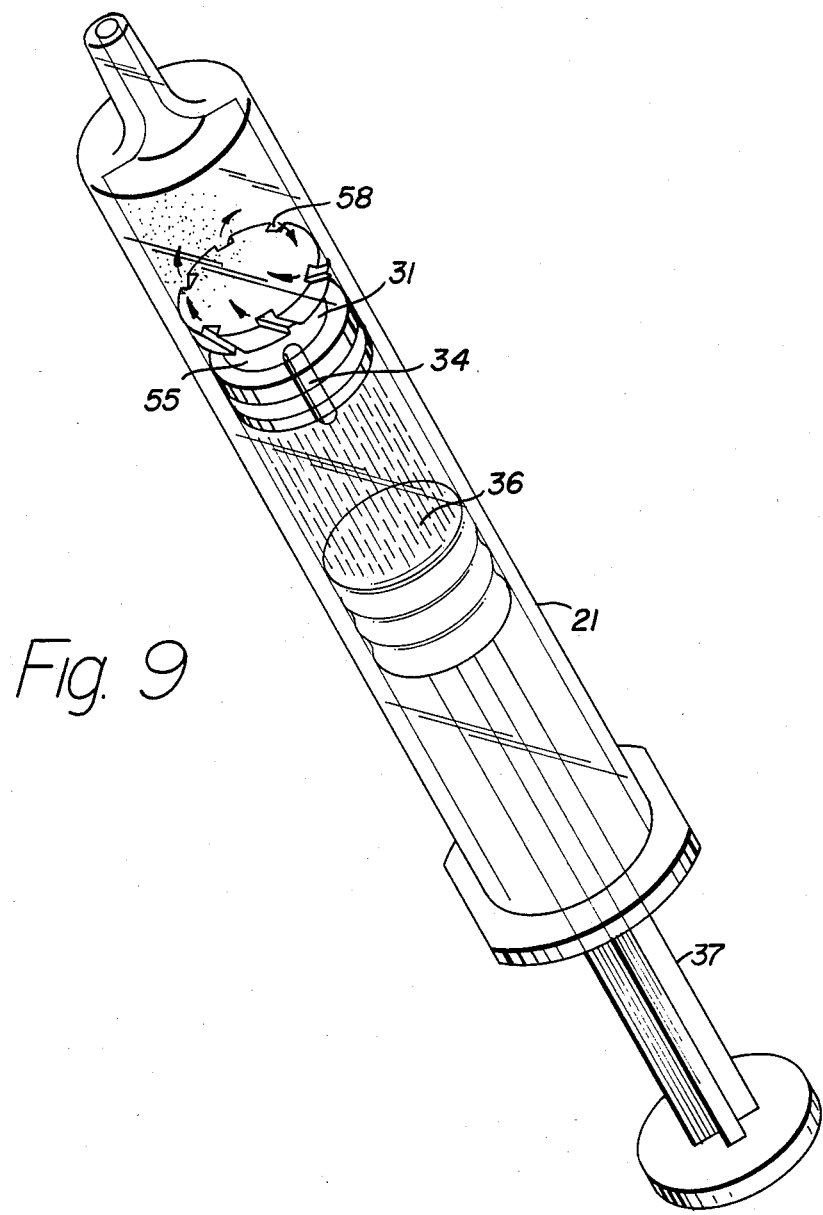
FIG. 9 is a perspective view of the syringe assembly of FIG. 4, schematically showing the mixing of the two medication components.
Figure 10:
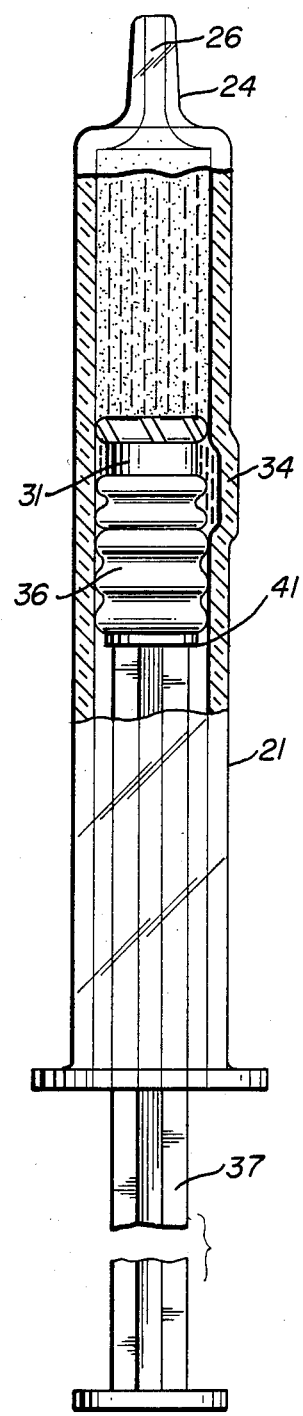
FIG. 10 is a side elevation view of the preferred two-component medication syringe assembly, with interior section partially exposed, showing the position of the piston and the by-pass stopper when the two components of the medication are fully mixed.

Mixing the first and second components of the medication, as best shown in FIGS. 7 through 9, is accomplished by removing the tip cap and orienting the syringe so that the tip faces in an upwardly direction as more specifically illustrated in FIG. 7. The user, while holding barrel 21 in one hand, pushes plunger rod 37 firmly in a direction toward the distal end of the barrel. Once the breakout force of the piston and the by-pass stopper is overcome, piston 36 will move toward the distal end of the syringe barrel, exerting pressure on first component 44, which in turn exerts pressure on by-pass stopper 31. The piston, first component of medication and the by-pass stopper will continue to move along the barrel until the proximal end of the by-pass stopper is positioned within by the by-pass zone, as best shown in FIG. 7. At this point, the pressure exerted on the liquid first component of the medication by piston 36 will force the liquid through by-pass passageway 35 between the by-pass and the by-pass stopper, around the proximal end of the by-pass stopper, into the area of the recess, then through grooves 58 into the area containing the second component of medication, as best illustrated in FIGS. 7 and 9. The orientation of the grooves in an angular direction with respect to the longitudinal axis of the stopper and the barrel causes liquid being forced through the grooves to be directed angularly with respect to the longitudinal axis, toward the inside surface of the barrel where the liquid tends to flow around the interior surface of the chamber causing a swirling action therein. This swirling action, as best illustrated in FIG. 9, facilitates the mixing of the two components of the medication. Also, the angularly positioned grooves preferably direct the liquid from the by-pass away from passageway 26 of the syringe barrel to minimize the possibility of liquid being expelled through the passageway during the mixing process and before all gases are expelled from the chamber. It should be noted that during the mixing process, if liquid is delivered into the passageway it will be expelled from the syringe when the gases in the chamber are expelled resulting in the loss of medication which is intended for injection into the patient. Also, loss of liquid through the passageway results in the undesirable change in the ratio of the two medication components. Prior art syringes have provided a barrier to prevent liquid escaping before mixing is complete, however, these barriers must later be punctured at the risk of producing potentially harmful particles or debris from the puncture, which can be injected into the patient.

Further motion of the by-pass stopper toward the distal end of the syringe barrel and liquid entering the distal end of the syringe barrel, through the grooves, will continue to displace any gases contained therein and force them out of the barrel via passageway 26. Pressure on the plunger rod is continued until piston 36 is adjacent to by-pass stopper 31 and all of the liquid component is substantially in distal chamber portion 32 between the distal end of the barrel and the by-pass stopper. At this point, the two components of the medication are mixed, or can be mixed by applying shaking forces to the barrel, and the medication is ready for injection. In this preferred embodiment, the combined volume of the first component and the second component of the medication, when mixed, is approximately equal to the volume defined within distal chamber portion 32 between the by-pass stopper and the distal end of the barrel, when the proximal end of the by-pass stopper is within the by-pass zone. It should be noted that the combined volume of the medication components, when the first component is a liquid and the second component is a powder, may be equal to or greater than the volume of the first liquid component depending on the chemical properties of the second powder component.

Figure 11:
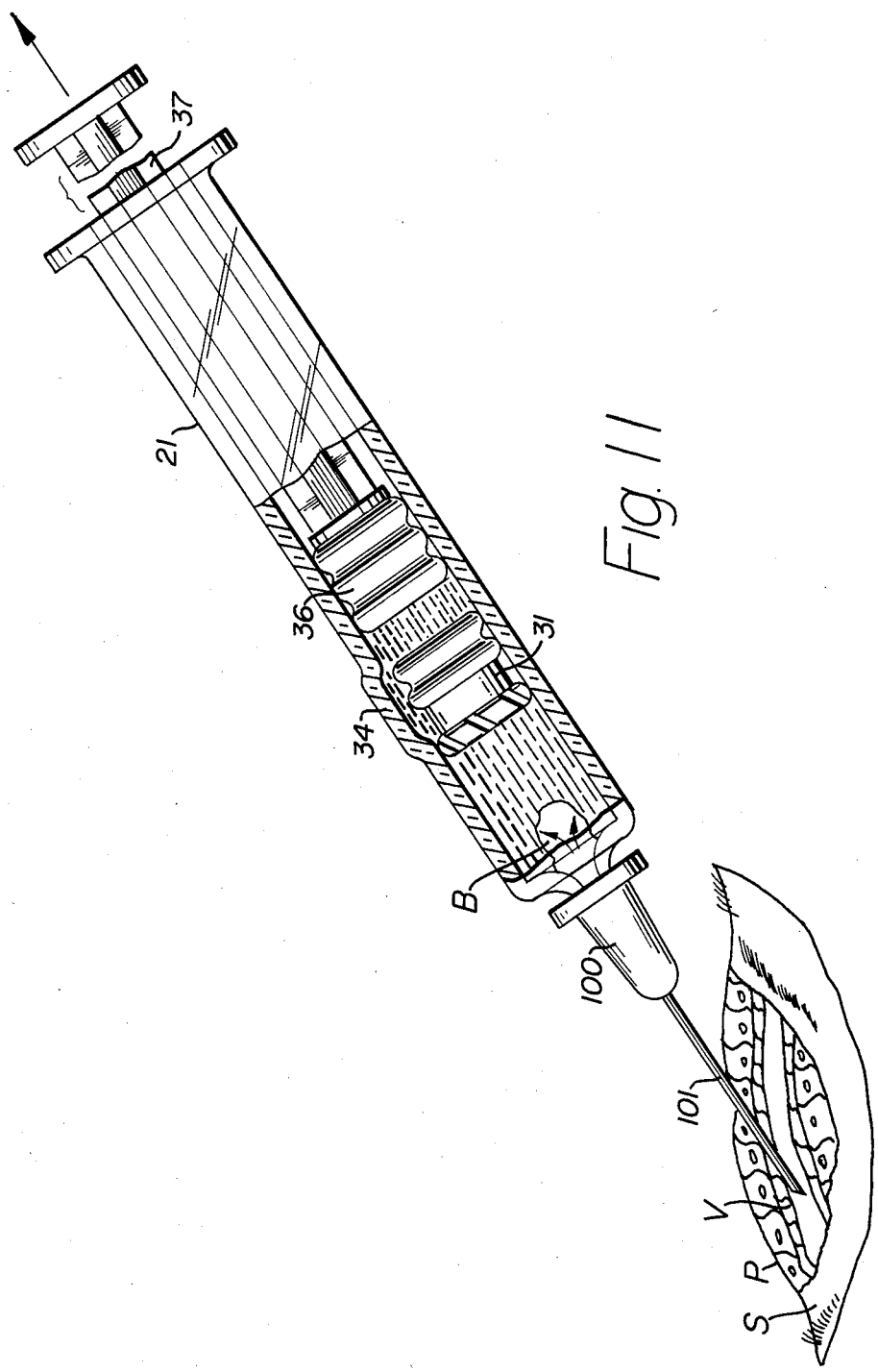
FIG. 11 is a side elevation view of the preferred two-component medication syringe assembly, with hypodermic needle assembly attached and interior section partially exposed, schematically showing the vein indication test.

Referring now to FIG. 11, injection of the medication into the vein of patient P requires the placement of a sterile hypodermic needle asembly 100 on the tip of the syringe barrel, and introducing sharp cannula 101 through the patient's skin S into vein V. To assure that the cannula is properly inserted in the vein, the plunger rod is withdrawn moving the piston 36 in that direction to create a reduced pressure zone inside the chamber which draws blood B from the vein into the chamber. The presence of blood in the chamber is visual evidence that the cannula is properly placed in a vein. The above described procedure for determining whether or not the cannula is properly placed in a vein is the vein indication test, as alluded to, above.

The vein indication test capacity of the preferred embodiment is facilitated because the volume of the components of the medication, when mixed, is approximately equal to the volume defined within distal chamber portion 32 between the by-pass stopper and the distal end of the barrel when the proximal end of the by-pass stopper is within the by-pass zone. This volumetric relationship allows the final precise positioning of the by-pass stopper by direct contact with piston 36 which is controlled by plunger rod 37. Most importantly, when withdrawing the plunger rod to perform the vein indication test, it is only necessary to move piston 36 and not by-pass stopper 31. Since only the piston is being moved, the force required to move the plunger rod is less, and there is less chance that the plunger rod will become disengaged from the piston.

The vein indication test should also be performed when injection of medication into a vein or artery is not desirable. In this case, the sharpened cannula of the hypodermic needle, connected to the syringe assembly, is made to pierce the injection site on the patient and the plunger rod is drawn away from the distal end of the syringe, moving piston 36 in that direction, to create a reduced pressure zone inside the chamber. The absence of blood in the chamber is visual evidence that the cannula is not improperly placed in a vein or artery.

When it is determined that the cannula is properly positioned in the patient, the medication may be injected, in the normal manner, by forcing the plunger rod toward the distal end of the barrel. The motion of plunger rod 37 forces piston 36 along the barrel, which in turn forces any liquid that may be between piston 36 and by-pass stopper 31 through the by-pass passageway into the distal chamber portion. At this point piston 36 is in contact with by-pass stopper 31 and motion of the plunger rod forces both the piston and the by-pass stopper along the barrel, thus forcing the medication through passageway 26, through cannula 101 and into the patient.

Referring now to FIGS. 12 through 14, an alternative syringe 63 of the instant invention includes a syringe barrel 60 having a chamber 61 for retaining fluid a tip 68 at the distal end of the barrel with a passageway 69 therethrough, a by-pass 62 represented by a raised peripheral portion of the barrel extending radially inwardly defining a by-pass zone along the barrel and a by-pass stopper 131, slidably positioned in fluid-tight engagement inside the barrel. Syringe 63 also includes piston 68 and plunger rod 69. The by-pass stopper includes a proximal end 152, a distal rib 154, a recess 155 and a groove 158 in the distal rib for allowing fluid communication between the recess and the chamber. Groove 158 is positioned in a substantially parallel relationship with respect to the longitudinal axis of the barrel so that liquid (not shown) passing through the groove is directed along the inside surface of the barrel in a substantially parallel relationship to the longitudinal axis of the barrel. The by-pass zone is shorter along the longitudinal axis of the barrel than the length of by-pass stopper 131 along the longitudinal axis of the barrel. The by-pass is sufficiently large and sufficiently raised to deflect the by-pass stopper so that when the proximal end of the by-pass stopper is in the by-pass zone, liquid can flow around the by-pass stopper between proximal end 152 and distal recess 155 through by-pass passageway 65. It is also within the purview of this embodiment to include multiple grooves around the periphery of the distal rib.

Adverting to FIGS. 15-17, another alternative syringe 80 of the present invention includes a syringe barrel 81 having a chamber 82 for retaining fluid and a by-pass (not shown). A tip 83 extends from the distal end of the barrel and contains a passageway 84 therethrough communicating with chamber 82. A needle 85 with a sharp distal end 86 and a lumen 87 is fixedly held in passageway 84, via epoxy, adhesive or other suitable means, so that the lumen is in fluid communication with chamber 82. Resilient needle shield 89 has an open end 90, a closed end 91 and a receptacle therein. The needle shield is removably attached to tip 83. Shield 89 is sized so that, when it is attached to the tip, sharp distal end 86 of the needle is preferably embedded in closed end 91 of the needle shield so that lumen 87, and therefore passageway 84, are sealed in an air tight arrangement. Removal of the shield exposes needle 85 and allows flow of fluid from chamber 82 through passageway 84 and lumen 87. The above-described structure eliminates the need for a separate hypodermic needle assembly.

The syringe barrel may be constructed of a wide variety of rigid materials such as metals, plastics and ceramics. Glass is preferred due to its transparency, low moisture vapor transmission rate and compatability with many medication formulations. A wide variety of materials, such as natural rubber, synthetic rubber and thermoplastic elastomers, are suitable for the piston, by-pass stopper and tip cap with natural rubber and butyl rubber being preferred. The choice of piston, by-pass stopper and tip cap material formulations will be highly dependent on compatability with the medication to be stored. A wide variety of materials, such as plastics and metals, are suitable for the plunger rod with thermoplastic materials such as polypropylene, polyethylene and polystryrene being preferred. It is preferred that all elements of the two-component medication syringe assembly be sterile when used. Accordingly, materials should be selected for compatibility with the sterilization process being used.

Thus, it can be seen that the present invention provides a simple, straightforward, reliable, easily fabricated syringe assembly, for the storage, mixing and administering of two-component medications. The instant invention minimizes contamination potential by allowing the mixing and administering steps to be performed without puncturing stoppers or other barriers within the syringe or transferring the medication components through barriers which are exterior to the syringe assembly. The preferred embodiment of the present invention provides a by-pass stopper that directs one component of the medication into the chamber containing the other component at an angle with respect to the longitudinal axis of the syringe barrel to promote a swirling action for enhancing the mixing of the two medication components and to minimize the potential of discharging medication through the syringe tip before mixing is complete and all gases are expelled from the syringe. The present invention also provides a two-component medication syringe assembly capable of performing the vein indication test.

What is claimed is:

1. A two-component mixing syringe comprising:
   an elongate, hollow barrel having a chamber for retaining the components;
   a tip extending from a distal end of said barrel having a passageway therethrough communicating with said chamber;
   a by-pass stopper slidably positioned in fluid-tight engagement inside said barrel having a distal rib contacting said barrel, said stopper having a recess on the proximal side of said rib and a groove in said rib, said groove allowing fluid communication between said recess and said chamber and positioned angularly with respect to the longitudinal axis of said barrel so that fluid passing through said groove is directed angularly with respect to the longitudinal axis of said barrel;
   a raised peripheral portion of said barrel serving as a by-pass and defining a by-pass zone, said by-pass zone being shorter than the length of said by-pass stopper along the longitudinal axis of said barrel, said by-pass being sufficiently long and raised to allow fluid to flow around said stopper between the proximal end of said stopper and said recess when the proximal end of said stopper is positioned in said by-pass zone; and
   a piston slidably positioned in fluid-tight engagement inside said barrel adapted to engage a plunger rod to facilitate its operation, said piston capable of moving fluid from said chamber through said passageway upon its movement toward said distal end, said piston capable of facilitating the drawing of fluid into said chamber through said passageway upon its movement away from said distal end.

2. The syringe of claim 1 wherein said groove is oriented at an angle within the range of about 30° to 80° with respect to the longitudinal axis of said barrel.

3. The syringe of claim 1 wherein said recess forms a continuous channel around the periphery of said stopper.

4. The syringe of claim 3 wherein there is a plurality of grooves all being in fluid communication with said recess.

5. The syringe of claim 4 wherein said grooves are substantially equally spaced from each other along the periphery of said distal rib.

6. The syringe of claim 1 further including at least one proximal rib on the proximal side of said recess contacting said barrel.

7. The syringe of claim 1 wherein said by-pass is positioned so that when said recess is in fluid communication with said by-pass and said distal rib is positioned outside of said by-pass zone, the volume defined within said chamber between said stopper and said distal end of said barrel is approximately the volume of the combined components.

8. The syringe of claim 1 wherein said by-pass is raised in an outwardly direction from said barrel.

9. The syringe of claim 1 further including sealing means for releasably sealing said passageway.

10. The syringe of claim 9 wherein said sealing means includes a tip cap removably held by said tip.

11. The syringe of claim 9 further including a first component in said chamber between said by-pass stopper and said piston, a second component in said chamber between said by-pass stopper and said distal end of said barrel, said by-pass stopper being positioned outside of said by-pass zone adjacent to the proximal end of said by-pass.

12. The syringe of claim 11 wherein said second component is a material selected from the group of medications consisting of liquid, powder, solids or combinations thereof.

13. The syringe of claim 1 wherein said by-pass stopper and said piston are made from material selected from the group consisting of natural rubber, synthetic rubber and thermoplastic elastomers.

14. The syringe of claim 1 further including a plunger rod engaged to said piston and extending outwardly from the proximal end of said barrel.

15. A two-component syringe comprising:
   a barrel having a chamber for retaining fluid;
   a distal end of said barrel having a passageway therethrough communicating with said chamber;
   a by-pass stopper slidably positioned in fluid-tight engagement inside said barrel having a distal rib, said stopper having a recess on the proximal side of said rib and fluid communication means in said rib for allowing fluid communication between said recess and said chamber, said fluid communication means being positioned so that fluid passing therethrough is directed angularly with respect to the longitudinal axis of said barrel;
   by-pass means for allowing fluid to flow around said stopper between the proximal end of said stopper and said recess; and
   piston means slidably positioned in fluid-tight engagement inside said barrel capable of engaging a plunger rod to facilitate its operation, said piston means capable of moving fluid from said chamber through said passageway upon its movement toward said distal end, said piston means capable of facilitating the drawing of fluid into said chamber through said passageway upon its movement away from said distal end.

16. The syringe of claim 15 wherein said fluid communication means is a groove.

17. A two-component medication syringe comprising:
   an elongate substantially cylindrical barrel having a chamber for retaining fluid;
   a tip extending from a distal end of said barrel having passageway therethrough communicating with said chamber, said tip having means for accepting a hypodermic needle;
   releasable sealing means associated with said tip for sealing said passageway;
   a by-pass stopper slidably positioned in fluid-tight engagement inside said barrel having a distal rib contacting said barrel, said stopper having a recess on the proximal side of said distal rib and a groove in said distal rib, said groove allowing fluid communication between said recess and said chamber, said groove positioned angularly with respect to the longitudinal axis of said barrel so that liquid passing through said groove is directed angularly with respect to the longitudinal axis of said barrel said stopper having at least one proximal rib on the proximal side of said recess contacting said barrel;

a raised peripheral portion of said barrel serving as a by-pass and defining a by-pass zone, said by-pass zone being shorter than the length of said by-pass stopper along the longitudinal axis of said barrel, said by-pass being sufficiently long and raised to allow liquid to flow around said by-pass stopper between the proximal end of said stopper and said recess when the proximal end of said stopper is positioned in said by-pass zone;

a piston slidably positioned in fluid-tight engagement inside said barrel adapted to engage a plunger rod to facilitate its operation, said piston capable of moving fluid from said chamber through said passageway upon its movement toward said distal end, said piston capable of facilitating the drawing of fluid into said chamber through said passageway upon its movement away from said distal end;

a first component of liquid medication contained within said chamber between said stopper and said piston, said stopper being positioned outside said by-pass zone adjacent to the proximal end of said by-pass; and a second component of medication substantially within said chamber between said stopper and said distal end of said barrel.

18. The syringe of claim 17 wherein said groove is oriented at an angle within the range of about 30° to 80° with respect to the longitudinal axis of said barrel.

19. The syringe of claim 18 wherein said recess forms a continuous channel around the periphery of said stopper.

20. The syringe of claim 19 wherein there is a plurality of grooves all being in fluid communication with said recess.

21. The syringe of claim 20 wherein said grooves are substantially equally spaced from each other along the periphery of said distal rib.

22. The syringe of claim 17 wherein said bypass is positioned so that when said recess is in fluid communication with said by-pass and said distal rib is positioned outside of said by-pass zone, the volume defined within said chamber between said stopper and said distal end of said barrel is approximately the volume of the combined components of the medication.

23. The syringe of claim 17 wherein said second component of medication is selected from the group of medications consisting of liquid, solid and powder.

24. A by-pass stopper for use in a syringe having a substantially cylindrical barrel comprising:

a piston-like body for slidable fluid tight engagement inside the barrel of a syringe having a first end, a second end and a longitudinal axis therethrough;

an annular rib at said first end and an annular rib at said second end of said body, said body having an annular recess between said ribs with a diameter less than the diameter of each of said ribs; and said rib at said first end having a plurality of grooves for allowing fluid communication therethrough, said grooves being positioned angularly with respect to said longitudinal axis.

25. The stopper of claim 24 further including a second rib adjacent to the rib on said second end of said body, said second rib having an outside diameter greater than the diameter of said recess.

26. The stopper of claim 24 wherein said grooves are oriented at an angle within the range of about 30° to 80° with respect to said longitudinal axis.

* * * * *